United States Patent
Wang et al.

(10) Patent No.: US 7,222,000 B2
(45) Date of Patent: May 22, 2007

(54) MOBILE VIDEOCONFERENCING PLATFORM WITH AUTOMATIC SHUT-OFF FEATURES

(75) Inventors: Yulun Wang, Goleta, CA (US); Charles S. Jordan, Santa Barbara, CA (US); Marco Pinter, Santa Barbara, CA (US); Jonathan Southard, Santa Barbara, CA (US)

(73) Assignee: InTouch Technologies, Inc., Goleta, CA (US)

( * ) Notice: Subject to any disclaimer, the term of this patent is extended or adjusted under 35 U.S.C. 154(b) by 369 days.

(21) Appl. No.: 11/039,341

(22) Filed: Jan. 18, 2005

(65) Prior Publication Data

US 2006/0161303 A1  Jul. 20, 2006

(51) Int. Cl.
*G06F 19/00* (2006.01)

(52) U.S. Cl. ............... 700/259; 700/247; 700/248; 700/251; 700/257; 700/258; 700/245; 700/260; 700/261; 700/262; 700/264; 318/568.11; 318/568.12; 318/568.13; 318/568.16; 318/568.21; 318/568.25; 606/1; 606/102; 606/130; 606/139; 600/117; 600/118; 600/407; 600/426; 600/429; 600/587; 600/595; 901/1; 901/2; 901/27

(58) Field of Classification Search ................. 700/259
See application file for complete search history.

(56) References Cited

U.S. PATENT DOCUMENTS

| | | |
|---|---|---|
| 3,821,995 A | 7/1974 | Aghnides |
| 4,413,693 A | 11/1983 | Derby |
| 4,471,354 A | 9/1984 | Smith |
| 4,519,466 A | 5/1985 | Shiraishi |
| 4,638,445 A | 1/1987 | Mattaboni |
| 4,733,737 A | 3/1988 | Falamak |
| 4,875,172 A | 10/1989 | Kanayama |
| 5,073,749 A | 12/1991 | Kanayama |

(Continued)

FOREIGN PATENT DOCUMENTS

CA  2289697 A1  11/1998

(Continued)

OTHER PUBLICATIONS

Yong et al., Robot task execution with teleprosence using virtual reality technology, 1998, Internet, p. 1-9.*

(Continued)

*Primary Examiner*—Thomas Black
*Assistant Examiner*—McDieunel Marc
(74) *Attorney, Agent, or Firm*—Ben J. Yorks; Irell & Manella LLP

(57) ABSTRACT

A remote controlled robot system that includes a robot and a remote control station. A user can control movement of the robot from the remote control station. The remote control station may generate robot control commands that are transmitted through a broadband network. The robot has a camera that generates video images that are transmitted to the remote control station through the network. The user can control movement of the robot while viewing the video images provided by the robot camera. The robot can automatically stop movement if it does not receive a robot control command within a time interval. The remote control station may transmit a stop command to the robot if the station does not receive an updated video image within a time interval.

23 Claims, 4 Drawing Sheets

U.S. PATENT DOCUMENTS

| | | |
|---|---|---|
| 5,186,270 A | 2/1993 | West |
| 5,341,854 A | 8/1994 | Zezulka et al. |
| 5,374,879 A | 12/1994 | Pin et al. |
| 5,419,008 A | 5/1995 | West |
| 5,544,649 A | 8/1996 | David et al. |
| 5,630,566 A | 5/1997 | Case |
| 5,636,218 A | 6/1997 | Ishikawa et al. |
| 5,762,458 A | 6/1998 | Wang et al. |
| 5,802,494 A | 9/1998 | Kuno |
| 5,838,575 A | 11/1998 | Lion |
| 5,857,534 A | 1/1999 | DeVault et al. |
| 5,959,423 A | 9/1999 | Nakanishi et al. |
| 5,966,130 A | 10/1999 | Benman, Jr. |
| 6,006,946 A | 12/1999 | Williams et al. |
| 6,036,812 A | 3/2000 | Williams et al. |
| 6,135,228 A | 10/2000 | Asada et al. |
| 6,232,735 B1 | 5/2001 | Baba et al. |
| 6,259,806 B1 | 7/2001 | Green |
| 6,292,713 B1 | 9/2001 | Jouppi et al. |
| 6,304,050 B1 | 10/2001 | Skaar et al. |
| 6,346,950 B1 | 2/2002 | Jouppi |
| 6,369,847 B1 | 4/2002 | James et al. |
| 6,430,471 B1 | 8/2002 | Kintou et al. |
| 6,438,457 B1 | 8/2002 | Yokoo et al. |
| 6,463,361 B1 | 10/2002 | Wang et al. |
| 6,474,434 B1 | 11/2002 | Bech |
| 6,491,701 B2 | 12/2002 | Tierney et al. |
| 6,496,099 B2 | 12/2002 | Wang et al. |
| 6,507,773 B2 * | 1/2003 | Parker et al. ............... 700/258 |
| 6,522,906 B1 | 2/2003 | Salisbury et al. |
| 6,535,793 B2 | 3/2003 | Allard |
| 6,549,215 B2 | 4/2003 | Jouppi |
| 6,587,750 B2 | 7/2003 | Gerbi et al. |
| 6,594,552 B1 | 7/2003 | Nowlin et al. |
| 6,684,129 B2 | 1/2004 | Salisbury et al. |
| 6,799,065 B1 | 9/2004 | Niemeyer |
| 6,804,656 B1 | 10/2004 | Rosenfeld et al. |
| 6,839,612 B2 | 1/2005 | Sanchez et al. |
| 6,845,297 B2 * | 1/2005 | Allard ........................ 700/259 |
| 7,174,238 B1 * | 2/2007 | Zweig ........................ 700/245 |
| 7,188,000 B2 * | 3/2007 | Chiappetta et al. ......... 700/245 |
| 2001/0037163 A1 | 11/2001 | Allard |
| 2001/0054071 A1 | 12/2001 | Loeb |
| 2002/0027597 A1 | 3/2002 | Sachau |
| 2002/0057279 A1 | 5/2002 | Jouppi |
| 2002/0058929 A1 | 5/2002 | Green |
| 2002/0063726 A1 | 5/2002 | Jouppi |
| 2002/0120362 A1 | 8/2002 | Lathan et al. |
| 2002/0130950 A1 | 9/2002 | James et al. |
| 2002/0141595 A1 | 10/2002 | Jouppi |
| 2002/0183894 A1 | 12/2002 | Wang et al. |
| 2003/0050733 A1 | 3/2003 | Wang et al. |
| 2003/0100892 A1 | 5/2003 | Morley et al. |
| 2003/0114962 A1 | 6/2003 | Niemeyer |
| 2003/0135203 A1 | 7/2003 | Wang et al. |
| 2003/0144649 A1 | 7/2003 | Ghodoussi et al. |
| 2003/0151658 A1 | 8/2003 | Smith |
| 2003/0220541 A1 | 11/2003 | Salisbury et al. |
| 2004/0019406 A1 | 1/2004 | Wang et al. |
| 2004/0117065 A1 | 6/2004 | Wang et al. |
| 2004/0143421 A1 | 7/2004 | Wang et al. |
| 2004/0162637 A1 | 8/2004 | Wang et al. |
| 2004/0167666 A1 | 8/2004 | Wang et al. |
| 2004/0167668 A1 | 8/2004 | Wang et al. |
| 2004/0174129 A1 | 9/2004 | Wang et al. |
| 2005/0021182 A1 | 1/2005 | Wang et al. |
| 2005/0021183 A1 | 1/2005 | Wang et al. |
| 2005/0021187 A1 | 1/2005 | Wang et al. |

FOREIGN PATENT DOCUMENTS

| | | |
|---|---|---|
| EP | 0981905 B1 | 1/2002 |
| JP | 07257422 | 10/1995 |
| JP | 2002-046088 | 2/2002 |
| JP | 2002305743 A | 10/2002 |

OTHER PUBLICATIONS

Bar-Cohen et al., Virtual reality robotic telesurgey, simulations using MEMICA haptic system, 2001, Internet, p. 1-7.*

Shimoga et al., Touch and force reflection for telpresence surgery, 1994, IEEE, p. 1049-1050.*

Baltus et al., "Towards Personal Service Robots for the Elderly", Computer Science and Robotoics.

Bauer, Jeffrey C., "Service Robots in Health Care: The Evolution of Mechanical Solutions to Human Resource Problems", Jun. 2003.

Breslow, Michael J., MD et al., "Effect of a multiple-site intensive care unit telemedicine program on climical and economic outcome: An alternative paradigm for intensivist staffing".

Celi et al., "The eICU: It's not just telemedicine", Critical Care Medicine, vol. 29, No. 8 (Supplement), Aug. 2001.

CNN.com/Technology, Paging R.Robot: Machine helps doctors with patients, 2003, Internet, 1-3.

Davies, "Robotics in Minimally Invasive Surgery", 1995, Internet, pp. 5/1-5/2.

Ellison et al., "Telerounding and Patient Satisfaction Following Surgery".

Goldman, Lea, "Machine Dreams", Entrepreneurs, Forbes, May 27, 2002.

Harmo et al., "Moving Eye—Interactive Telepresence Over Internet With a Ball Shaped Mobile Robot", 2000.

Hees, William P., "Communications Design for a Remote Presence Robot", Jan. 14, 2002.

Jouppi, et al., :Mutually-Immersive Audio Telepresence, Audio Engineering Society Convention Paper, presented at 113th Convention Oct. 2002.

Jouppi, Norman P., "First Steps Towards Mutually-Immersive Mobile Telepresence", 2002.

Kanehiro, Fumio et al., Virtual Humanoid Robot Platform to Develop Controllers of Real Humanoid Robots without Porting, 2001, IEEE, pp. 3217-3276.

Kaplan et al., "An Internet Accessible Telepresence".

Kuzuoka et al., "Can The GestureCam Be A Surrogate?".

Lim, Hun-ok et al., Control to Realize Human-Like Walking of a Biped Humanoid Robot, IEE 2000, pp. 3271-3276.

Loeb, Gerald, "Virtual Visit: Improving Communication for Those Who Need It Most", 2001.

Mack, "Minimally invasive and robotic surgery", 2001, IEEE, pp. 568-572.

Magne Charge—Smart Power for Electric Vehicles, Internet 2002.

Martin, Anya, "Days Ahead", Assisted Living Today, vol. 9, Nov./Dec. 2002, pp. 19-22.

McCardle et al., "The challenge of utilizing new technology in design education", 2000 Internet, pp. 122-127.

Ojha, Anad, "An application of Virtual Reality in Rehabilitation", Jan. 1994, IEEE, pp. 4-6.

Paulos et al., "A World Wide Web Telerobotic Remote Environment Browser", http://vive.cs.berkeley.edu/capek, 1995.

Paulos, Eric John, "Personal Tele-Embodiment", 2001.

Paulos, et al. , "Ubiquitous Tele-embodiment: Applications and Implications", International Journal of Human Computer Studies, Jun. 1997, vol. 46, No. 6, pp. 861-877.

Paulos, et al., "Designing Personal Tele-Embodiment", Presented at the IEEE International Conference on Robotics and Animation, Leuven, Belgium, May 20, 1998.

Pin et al., "A New Family of Omnidirectional and Holonomic Wheeled Platforms for Mobile Robots", IEEE, vol. 10, No. 4, Aug. 1994.

Roland Piquepaille's Technology Trends, How new technologies are modifying your way of life, 2003, Internet, pp. 1-2.

PYXIS HelpMate®, the Trackless Robotic Courier, Internet, 3 pgs.

"Remote Presence", p. 131-147.
Roy et al., "Towards Personal Service Robots for the Elderly", Internet 2002.
Stephenson, Gary, "Dr. Robot Tested at Hopkins", 2003, Internet, p. 1.
Stoianovici et al., "Robotic Tools for Minimally Invasive Urologic Surgery", 2002, Internet, 1-17.
Tendick et al., "Human-Machine Interfaces for Minimally Invasive Surgery", 1997, IEEE, pp. 1-6.
Thrun et al, "Probabilistic Algorithms and the Interactive Museum Tour-Guide Robot Minerva", 2000, Internet pp. 1-35.
Tzafestas, et al., "VR-based Teleoperation of a Mobile Robotic Assistant: Progress Report", 2000, Internet, pp. 1-23.
Urquhart, Kim, "InTouch's robotic Companion 'beams up' healthcare experts", Medical Device Daily, vol. 7, No. 39, Feb. 27, 2003, p. 1,4.
Zorn, Benjamin G., "Ubiquitous Telepresence", http://www.cs.colorado.edu/~zorn/ut/vision/vison.html., Mar. 5, 1996.

* cited by examiner

MOBILE VIDEOCONFERENCING PLATFORM WITH AUTOMATIC SHUT-OFF FEATURES

BACKGROUND OF THE INVENTION

1. Field of the Invention

The subject matter disclosed generally relates to the field of mobile two-way teleconferencing.

2. Background Information

Robots have been used in a variety of applications ranging from remote control of hazardous material to assisting in the performance of surgery. For example, U.S. Pat. No. 5,762,458 issued to Wang et al. discloses a system that allows a surgeon to perform minimally invasive medical procedures through the use of robotically controlled instruments. One of the robotic arms in the Wang system moves an endoscope that has a camera. The camera allows a surgeon to view a surgical area of a patient.

Tele-robots such as hazardous waste handlers and bomb detectors may contain a camera that allows the operator to view the remote site. Canadian Pat. No. 2289697 issued to Treviranus, et al. discloses a teleconferencing platform that has both a camera and a monitor. The platform includes mechanisms to both pivot and raise the camera and monitor. The Treviranus patent also discloses embodiments with a mobile platform, and different mechanisms to move the camera and the monitor.

There has been marketed a mobile robot introduced by InTouch Technologies, Inc., the assignee of this application, under the trademarks COMPANION and RP-6. The InTouch robot is controlled by a user at a remote station. The remote station may be a personal computer with a joystick that allows the user to remotely control the movement of the robot. Both the robot and remote station have cameras, monitors, speakers and microphones to allow for two-way video/audio communication. The robot camera provides video images to a screen at the remote station so that the user can view the robot's surroundings and move the robot accordingly.

The InTouch robot system typically utilizes a broadband network such as the Internet to establish the communication channel between the remote station and the robot. For various reasons the network may not always reliably transmit information between the remote station and the robot. For example, the remote station may transmit control commands to the robot that are never received. The control commands may be instructions to avoid a person or object. If the commands are not received the robot may hit the person/object. Additionally, updated video images from the robot may not be received by the remote station. The user is thus viewing outdated video images and may send commands that cause the robot to hit a person or object. It would be desirable to provide functions within the system to stop the robot in the event of transmission errors between the robot and remote station.

BRIEF SUMMARY OF THE INVENTION

A remote controlled robot system that includes a robot and a remote control station. The robot moves in response to robot control commands transmitted by the remote control station. The robot can automatically stop movement if a robot control command is not received within a time interval. The remote control station may transmit a stop command to the robot if the station does not receive a video image from a robot camera within a time interval.

DETAILED DESCRIPTION

Disclosed is a remote controlled robot system that includes a robot and a remote control station. A user can control movement of the robot from the remote control station. The remote control station may generate robot control commands that are transmitted through a broadband network. The robot has a camera that generates video images that are transmitted to the remote control station through the network. The user can control movement of the robot while viewing the video images provided by the robot camera. The robot can automatically stop movement if it does not receive a robot control command within a time interval. The remote control station may transmit a stop command to the robot if the station does not receive an updated video image within a time interval.

Stopping the robot if there are no control commands, or updated video images provides safety features that compensate for transmission errors. For example, the automatic stop feature prevents undesirable robot movement in the event robot control commands are not properly transmitted. Additionally, the generation of a stop command by the remote station insures that the user is not moving the robot based on a erroneous video image.

Figure 1:
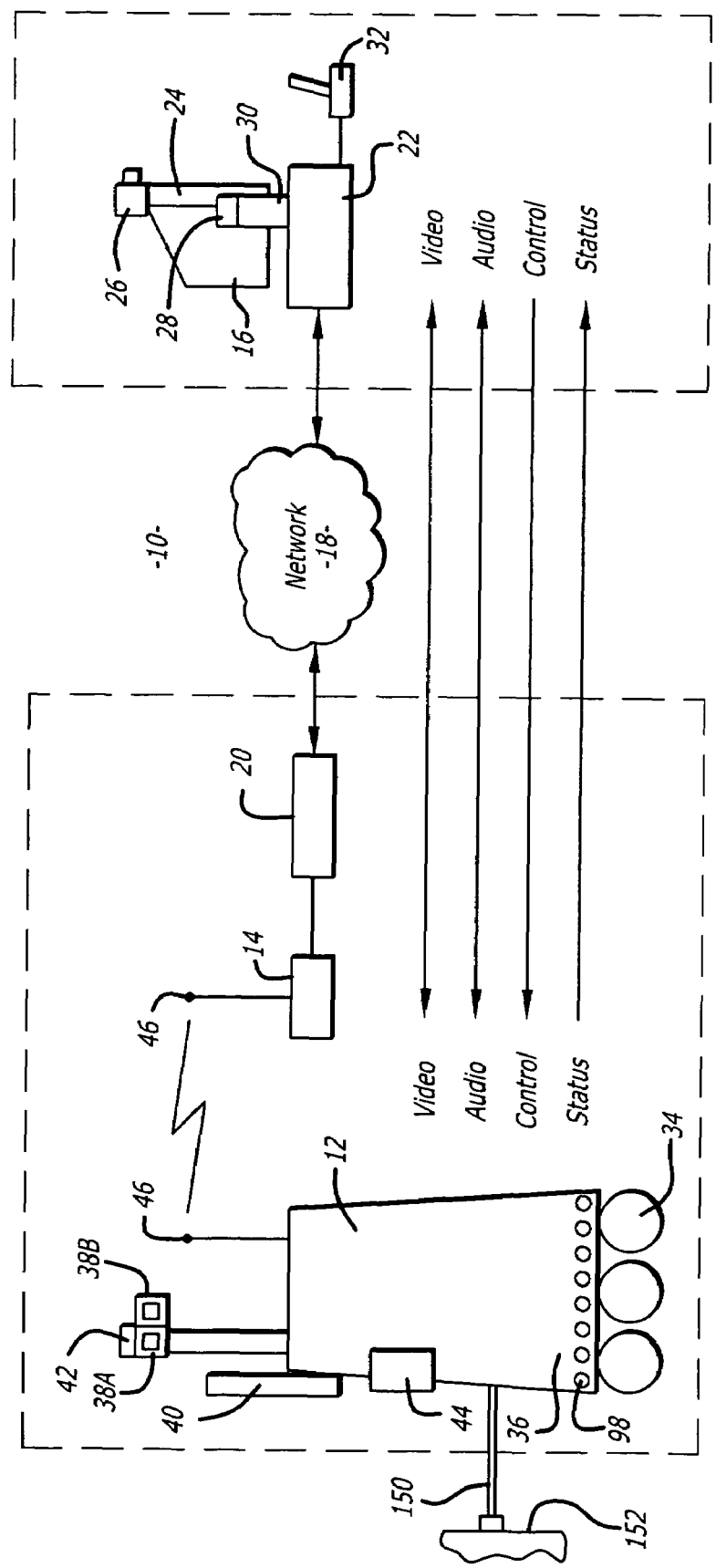
FIG. 1 is an illustration of a robotic system.

Referring to the drawings more particularly by reference numbers, FIG. 1 shows a robotic system 10 that can be used to conduct a remote visit. The robotic system 10 includes a robot 12, a base station 14 and a remote control station 16. The remote control station 16 may be coupled to the base station 14 through a network 18. By way of example, the network 18 may be either a packet switched network such as the Internet, or a circuit switched network such has a Public Switched Telephone Network (PSTN) or other broadband system. The base station 14 may be coupled to the network 18 by a modem 20 or other broadband network interface device. By way of example, the base station 14 may be a wireless router. Alternatively, the robot 12 may have a direct connection to the network thru for example a satellite.

The remote control station 16 may include a computer 22 that has a monitor 24, a camera 26, a microphone 28 and a speaker 30. The computer 22 may also contain an input device 32 such as a joystick or a mouse. The control station 16 is typically located in a place that is remote from the robot 12. Although only one remote control station 16 is shown, the system 10 may include a plurality of remote stations. In general any number of robots 12 may be controlled by any number of remote stations 16 or other robots 12. For example, one remote station 16 may be coupled to a plurality of robots 12, or one robot 12 may be coupled to a plurality of remote stations 16, or a plurality of robots 12.

Each robot 12 includes a movement platform 34 that is attached to a robot housing 36. Also attached to the robot housing 36 is a pair of cameras 38, a monitor 40, a microphone(s) 42 and a speaker(s) 44. The microphone 42 and speaker 30 may create a stereophonic sound. The robot 12 may also have an antenna 46 that is wirelessly coupled to an antenna 48 of the base station 14. The system 10 allows a user at the remote control station 16 to move the robot 12 through operation of the input device 32. The robot camera 38 is coupled to the remote monitor 24 so that a user at the remote station 16 can view a patient. Likewise, the robot monitor 40 is coupled to the remote camera 26 so that the patient can view the user. The microphones 28 and 42, and speakers 30 and 44, allow for audible communication between the patient and the user.

The remote station computer 22 may operate Microsoft OS software and WINDOWS XP or other operating systems such as LINUX. The remote computer 22 may also operate a video driver, a camera driver, an audio driver and a joystick driver. The video images may be transmitted and received with compression software such as MPEG CODEC.

Figure 2:
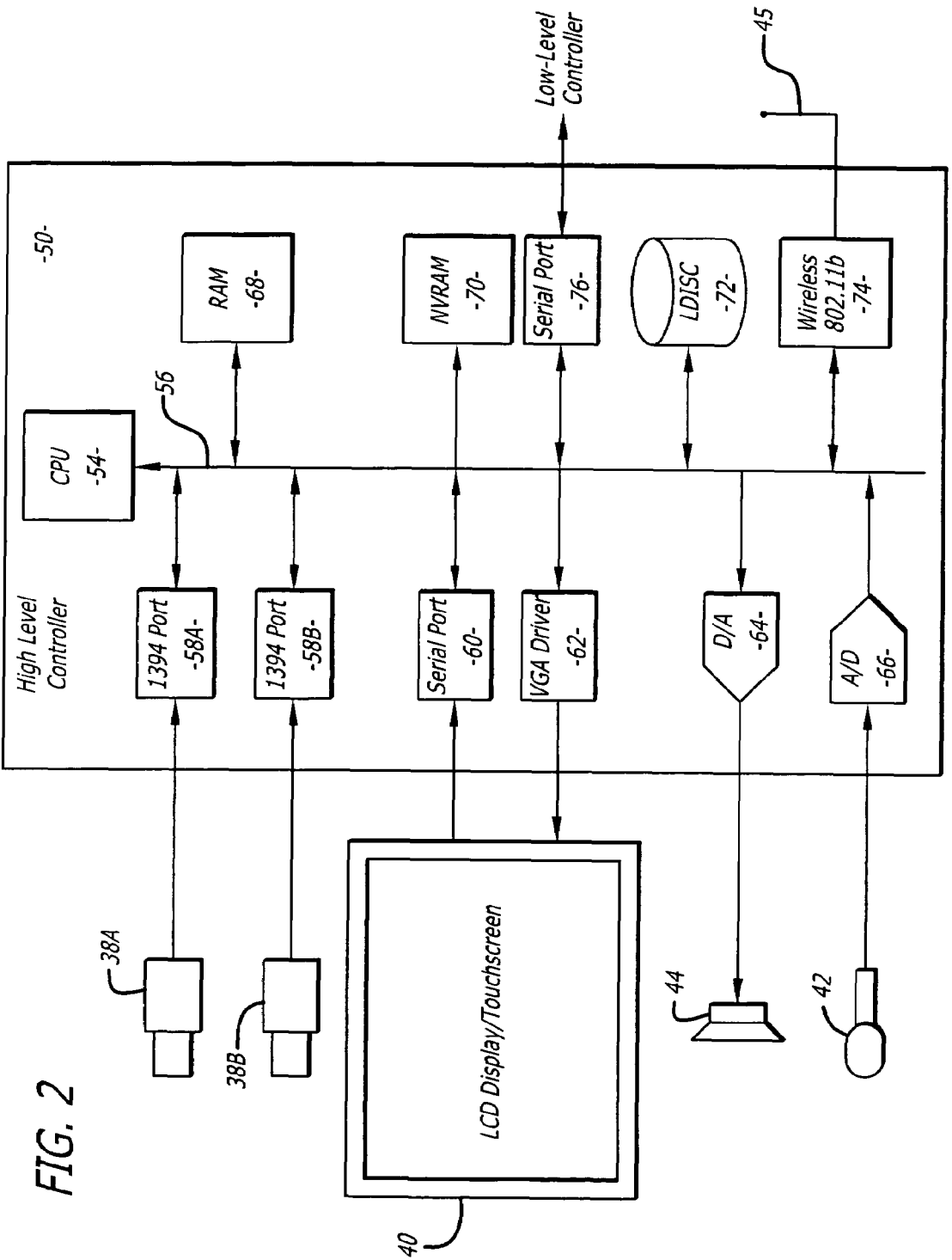
FIG. 2 is a schematic of an electrical system of a robot.
Figure 3:
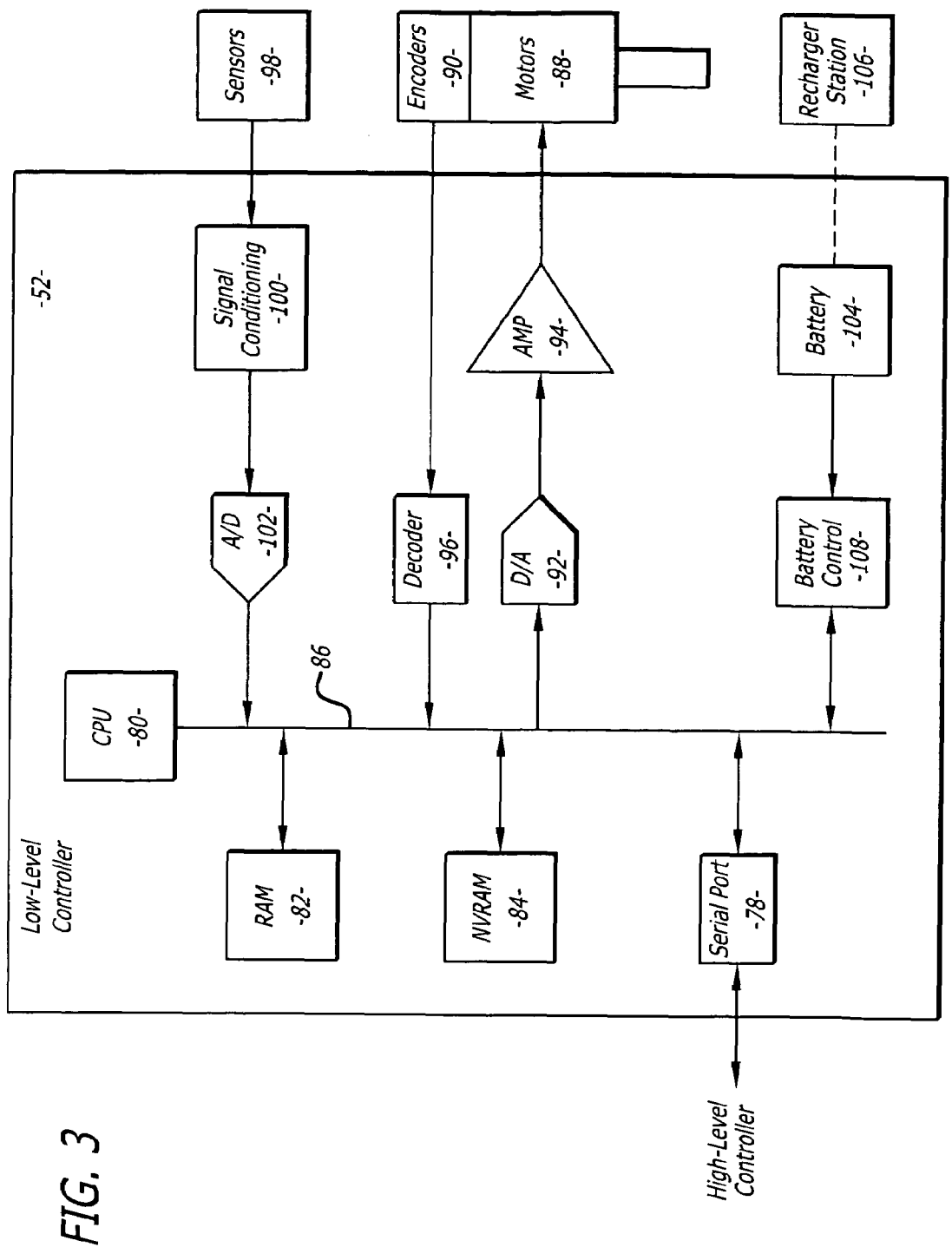
FIG. 3 is a further schematic of the electrical system of the robot.

FIGS. 2 and 3 show an embodiment of a robot 12. Each robot 12 may include a high level control system 50 and a low level control system 52. The high level control system 50 may include a processor 54 that is connected to a bus 56. The bus 56 is coupled to the camera 38 by an input/output (I/O) ports 58. The monitor 40 is coupled to the bus 56 by a serial output port 60 and a VGA driver 62. The monitor 40 may include a touchscreen function that allows the patient to enter input by touching the monitor screen.

The speaker 44 is coupled to the bus 56 by a digital to analog converter 64. The microphone 42 is coupled to the bus 56 by an analog to digital converter 66. The high level controller 50 may also contain random access memory (RAM) device 68, a non-volatile RAM device 70 and a mass storage device 72 that are all coupled to the bus 62. The mass storage device 72 may contain medical files of the patient that can be accessed by the user at the remote control station 16. For example, the mass storage device 72 may contain a picture of the patient. The user, particularly a health care provider, can recall the old picture and make a side by side comparison on the monitor 24 with a present video image of the patient provided by the camera 38. The robot antennae 45 may be coupled to a wireless transceiver 74. By way of example, the transceiver 74 may transmit and receive information in accordance with IEEE 802.11b.

The controller 54 may operate with a LINUX OS operating system. The controller 54 may also operate MS WINDOWS along with video, camera and audio drivers for communication with the remote control station 16. Video information may be transceived using MPEG CODEC compression techniques. The software may allow the user to send e-mail to the patient and vice versa, or allow the patient to access the Internet. In general the high level controller 50 operates to control communication between the robot 12 and the remote control station 16.

The remote control station 16 may include a computer that is similar to the high level controller 50. The computer would have a processor, memory, I/O, software, firmware, etc. for generating, transmitting, receiving and processing information.

The high level controller 50 may be linked to the low level controller 52 by serial ports 76 and 78. The low level controller 52 includes a processor 80 that is coupled to a RAM device 82 and non-volatile RAM device 84 by a bus 86. Each robot 12 contains a plurality of motors 88 and motor encoders 90. The motors 88 can actuate the movement platform and move other parts of the robot such as the monitor and camera. The encoders 90 provide feedback information regarding the output of the motors 88. The motors 88 can be coupled to the bus 86 by a digital to analog converter 92 and a driver amplifier 94. The encoders 90 can be coupled to the bus 86 by a decoder 96. Each robot 12 also has a number of proximity sensors 98 (see also FIG. 1). The position sensors 98 can be coupled to the bus 86 by a signal conditioning circuit 100 and an analog to digital converter 102.

The low level controller 52 runs software routines that mechanically actuate the robot 12. For example, the low level controller 52 provides instructions to actuate the movement platform to move the robot 12. The low level controller 52 may receive movement instructions from the high level controller 50. The movement instructions may be received as movement commands from the remote control station or another robot. Although two controllers are shown, it is to be understood that each robot 12 may have one controller, or more than two controllers, controlling the high and low level functions.

The various electrical devices of each robot 12 may be powered by a battery(ies) 104. The battery 104 may be recharged by a battery recharger station 106 (see also FIG. 1). The low level controller 52 may include a battery control circuit 108 that senses the power level of the battery 104. The low level controller 52 can sense when the power falls below a threshold and then send a message to the high level controller 50.

The system may be the same or similar to a robotic system provided by the assignee InTouch-Health, Inc. of Santa Barbara, Calif. under the name RP-6. The system may also be the same or similar to the system disclosed in application Ser. No. 10/206,457 published on Jan. 29, 2004, which is hereby incorporated by reference.

Figure 4:
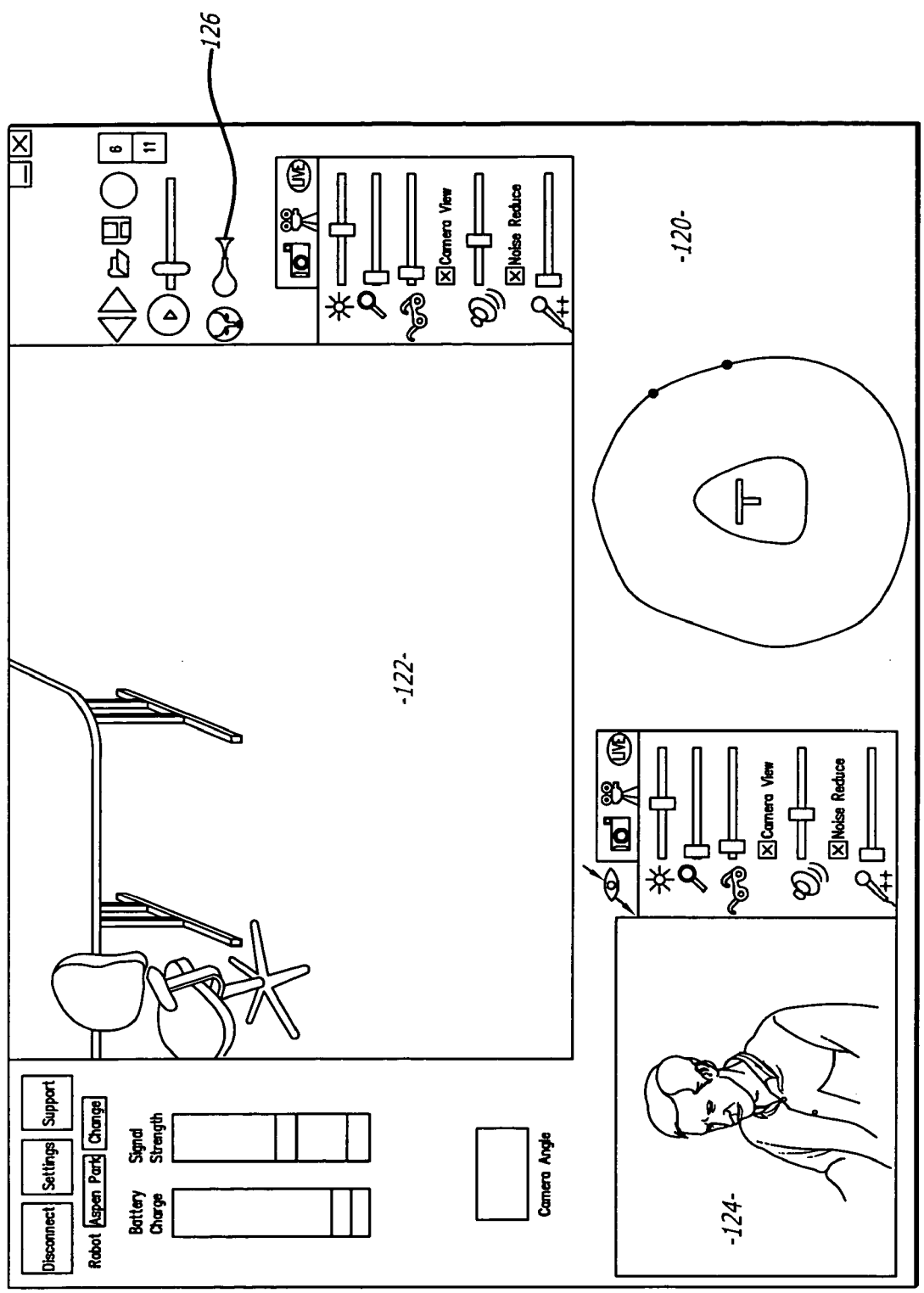
FIG. 4 is a graphical user interface of a remote station.

FIG. 4 shows a display user interface ("DUI") 120 that can be displayed at the remote station 16. The DUI 120 may include a robot view field 122 that displays a video image provided by the camera of the robot. The DUI 120 may also include a station view field 124 that displays a video image provided by the camera of the remote station 16. The DUI 120 may be part of an application program stored and operated by the computer 22 of the remote station 16.

The DUI 120 may include alert input icons 126 and 128. Alert icon 126 can be selected by the user at the remote station to generate an alert indicator such as a sound from the speaker of the robot. Selection of the icon generates an alert input to the robot. The robot generates a sound through its speaker in response to the alert input. By way of example, the sound may simulate the noise of a horn. Consequently, the icon may have the appearance of a horn. The remote station user may select the horn shaped icon 126 while remotely moving the robot to alert persons to the presence of the moving robot.

Alert icon 128 can be selected to request access to the video images from the robot. The default state of the robot may be to not send video information to the remote station. Selecting the alert icon 128 sends an alert input such as an access request to the robot. The robot then generates an alert indicator. The alert indicator can be a sound generated by the robot speaker, and/or a visual prompt on the robot monitor. By way of example, the visual prompt may be a "flashing" graphical icon. The sound may simulate the knocking of a door. Consequently, the alert icon 128 may have the appearance of a door knocker.

In response to the alert indicator the user may provide a user input such as the depression of a button on the robot, or the selection of a graphical image on the robot monitor, to allow access to the robot camera. The robot may also have a voice recognition system that allows the user to grant access with a voice command. The user input causes the robot to begin transmitting video images from the robot camera to the remote station that requested access to the robot. A voice communication may be established before the cycle of the alert input and response, to allow the user at the remote station to talk to the caller recipient at the robot.

In operation, the robot 12 may be placed in a home or a facility where one or more patients are to be monitored and/or assisted. The facility may be a hospital or a residential care facility. By way of example, the robot 12 may be placed in a home where a health care provider may monitor and/or assist the patient. Likewise, a friend or family member may communicate with the patient. The cameras and monitors at both the robot and remote control stations allow for teleconferencing between the patient and the person at the remote station(s).

The robot 12 can be maneuvered through the home or a facility by manipulating the input device 32 at a remote station 16. The robot 10 may be controlled by a number of different users. To accommodate for this the robot may have an arbitration system. The arbitration system may be integrated into the operating system of the robot 12. For example, the arbitration technique may be embedded into the operating system of the high-level controller 50.

By way of example, the users may be divided into classes that include the robot itself, a local user, a caregiver, a doctor, a family member, or a service provider. The robot 12 may override input commands that conflict with robot operation. For example, if the robot runs into a wall, the system may ignore all additional commands to continue in the direction of the wall. A local user is a person who is physically present with the robot. The robot could have an input device that allows local operation. For example, the robot may incorporate a voice recognition system that receives and interprets audible commands.

A caregiver is someone who remotely monitors the patient. A doctor is a medical professional who can remotely control the robot and also access medical files contained in the robot memory. The family and service users remotely access the robot. The service user may service the system such as by upgrading software, or setting operational parameters.

The robot 12 may operate in one of two different modes; an exclusive mode, or a sharing mode. In the exclusive mode only one user has access control of the robot. The exclusive mode may have a priority assigned to each type of user. By way of example, the priority may be in order of local, doctor, caregiver, family and then service user. In the sharing mode two or more users may share access with the robot. For example, a caregiver may have access to the robot, the caregiver may then enter the sharing mode to allow a doctor to also access the robot. Both the caregiver and the doctor can conduct a simultaneous teleconference with the patient.

The arbitration scheme may have one of four mechanisms; notification, timeouts, queue and call back. The notification mechanism may inform either a present user or a requesting user that another user has, or wants, access to the robot. The timeout mechanism gives certain types of users a prescribed amount of time to finish access to the robot. The queue mechanism is an orderly waiting list for access to the robot. The call back mechanism informs a user that the robot can be accessed. By way of example, a family user may receive an e-mail message that the robot is free for usage. Tables I and II, show how the mechanisms resolve access request from the various users.

TABLE I

| User | Access Control | Medical Record | Command Override | Software/Debug Access | Set Priority |
|---|---|---|---|---|---|
| Robot | No | No | Yes (1) | No | No |
| Local | No | No | Yes (2) | No | No |
| Caregiver | Yes | Yes | Yes (3) | No | No |
| Doctor | No | Yes | No | No | No |
| Family | No | No | No | No | No |
| Service | Yes | No | Yes | Yes | Yes |

TABLE II

| | Requesting User | | | | |
|---|---|---|---|---|---|
| | Local | Caregiver | Doctor | Family | Service |
| Current User | | | | | |
| Local | Not Allowed | Warn current user of pending user Notify requesting user that system is in use Set timeout | Warn current user of pending user Notify requesting user that system is in use Set timeout = 5 m | Warn current user of pending user Notify requesting user that system is in use Set timeout = 5 m Call back | Warn current user of pending user Notify requesting user that system is in use No timeout Call back |
| Caregiver | Warn current user of pending user. Notify requesting user that system is in use. Release control | Not Allowed | Warn current user of pending user Notify requesting user that system is in use Set timeout = 5 m Queue or callback | Warn current user of pending user Notify requesting user that system is in use Set timeout = 5 m | Warn current user of pending user Notify requesting user that system is in use No timeout Callback |
| Doctor | Warn current user of pending user Notify requesting user that system is in use Release control | Warn current user of pending user Notify requesting user that system is in use Set timeout = 5 m | Warn current user of pending user Notify requesting user that system is in use No timeout Callback | Notify requesting user that system is in use No timeout Queue or callback | Warn current user of pending user Notify requesting user that system is in use No timeout Callback |
| Family | Warn current user of pending user | Notify requesting user that system is in | Warn current user of pending user | Warn current user of pending user | Warn current user of pending user |

TABLE II-continued

| | | Requesting User | | | |
|---|---|---|---|---|---|
| | Local | Caregiver | Doctor | Family | Service |
| | Notify requesting user that system is in use Release Control | use No timeout Put in queue or callback | Notify requesting user that system is in use Set timeout = 1 m | Notify requesting user that system is in use Set timeout = 5 m Queue or callback | Notify requesting user that system is in use No timeout Callback |
| Service | Warn current user of pending user Notify requesting user that system is in use No timeout | Notify requesting user that system is in use No timeout Callback | Warn current user of request Notify requesting user that system is in use No timeout Callback | Warn current user of pending user Notify requesting user that system is in use No timeout Queue or callback | Not Allowed |

The information transmitted between the station 16 and the robot 12 may be encrypted. Additionally, the user may have to enter a password to enter the system 10. A selected robot is then given an electronic key by the station 16. The robot 12 validates the key and returns another key to the station 16. The keys are used to encrypt information transmitted in the session.

The robot 12 and remote station 16 transmit commands through the broadband network 18. The commands can be generated by the user in a variety of ways. For example, commands to move the robot may be generated by moving the joystick 32 (see FIG. 1). The commands are preferably assembled into packets in accordance with TCP/IP protocol. Table III provides a list of control commands that are generated at the remote station and transmitted to the robot through the network.

TABLE III

Control Commands

| Command | Example | Description |
|---|---|---|
| drive | drive 10.0 0.0 5.0 | The drive command directs the robot to move at the specified velocity (in cm/sec) in the (x, y) plane, and turn its facing at the specified rate (degrees/sec). |
| goodbye | goodbye | The goodbye command terminates a user session and relinquishes control of the robot |
| gotoHomePosition | gotoHomePosition 1 | The gotoHomePosition command moves the head to a fixed "home" position (pan and tilt), and restores zoom to default value. The index value can be 0, 1, or 2. The exact pan/tilt values for each index are specified in robot configuration files. |
| head | head vel pan 5.0 tilt 10.0 | The head command controls the head motion. It can send commands in two modes, identified by keyword: either positional ("pos") or velocity ("vol"). In velocity mode, the pan and tilt values are desired velocities of the head on the pan and tilt axes, in degree/sec. A single command can include just the pan section, or just the tilt section, or both. |
| keepalive | keepalive | The keepalive command causes no action, but keeps the communication (socket) link open so that a session can continue. In scripts, it can be used to introduce delay time into the action. |
| odometry | odometry 5 | The odometry command enables the flow of odometry messages from the robot. The argument is the number of times odometry is to be reported each second. A value of 0 turns odometry off. |
| reboot | reboot | The reboot command causes the robot computer to reboot immediately. The ongoing session is immediately broken off. |
| restoreHeadPosition | restoreHeadPosition | The restoreHeadPosition functions like the gotoHomePosition command, but it homes the head to a position previously saved with gotoHomePosition. |
| saveHeadPosition | saveHeadPosition | The saveHeadPosition command causes the robot to save the current head position (pan |

TABLE III-continued

Control Commands

| Command | Example | Description |
|---|---|---|
| | | and tilt) in a scratch location in temporary storage so that this position can be restored. Subsequent calls to "restoreHeadPosition" will restore this saved position. Each call to saveHeadPosition overwrites any previously saved position. |
| setCameraFocus | setCameraFocus 100.0 | The setCameraFocus command controls focus for the camera on the robot side. The value sent is passed "raw" to the video application running on the robot, which interprets it according to its own specification. |
| setCameraZoom | setCameraZoom 100.0 | The setCameraZoom command controls zoom for the camera on the robot side. The value sent is passed "raw" to the video application running on the robot, which interprets it according to its own specification. |
| shutdown | Shutdown | The shutdown command shuts down the robot and powers down its computer. |
| stop | stop | The stop command directs the robot to stop moving immediately. It is assumed this will be as sudden a stop as the mechanism can safely accommodate. |
| timing | Timing 3245629 500 | The timing message is used to estimate message latency. It holds the UCT value (seconds + milliseconds) of the time the message was sent, as recorded on the sending machine. To do a valid test, you must compare results in each direction (i.e., sending from machine A to machine B, then from machine B to machine A) in order to account for differences in the clocks between the two machines. The robot records data internally to estimate average and maximum latency over the course of a session, which it prints to log files. |
| userTask | userTask "Jane Doe" "Remote Visit" | The userTask command notifies the robot of the current user and task. It typically is sent once at the start of the session, although it can be sent during a session if the user and/or task change. The robot uses this information for record-keeping. |

Table IV provides a list of reporting commands that are generated by the robot and transmitted to the remote station through the network.

TABLE IV

Reporting Commands

| Command | Example | Description |
|---|---|---|
| abnormalExit | abnormalExit | This message informs the user that the robot software has crashed or otherwise exited abnormally. Te robot software catches top-level exceptions and generates this message if any such exceptions occur. |
| bodyType | bodyType 3 | The bodyType message informs the station which type body (using the numbering of the mechanical team) the current robot has. This allows the robot to be drawn correctly in the station user interface, and allows for any other necessary body-specific adjustments. |
| driveEnabled | driveEnabled true | This message is sent at the start of a session to indicate whether the drive system is operational. |

TABLE IV-continued

Reporting Commands

| Command | Example | Description |
| --- | --- | --- |
| emergencyShutdown | emergencyShutdown | This message informs the station that the robot software has detected a possible "runaway" condition (an failure causing the robot to move out of control) and is shutting the entire system down to prevent hazardous motion. |
| odometry | odometry 10 20 340 | The odometry command reports the current (x, y) position (cm) and body orientation (degrees) of the robot, in the original coordinate space of the robot at the start of the session. |
| sensorGroup | group_data | Sensors on the robot are arranged into groups, each group of a single type (bumps, range sensors, charge meter, etc.) The sensorGroup message is sent once per group at the start of each session. It contains the number, type, locations, and any other relevant data for the sensors in that group. The station assumes nothing about the equipment carried on the robot; everything it knows about the sensors comes from the sensorGroup messages. |
| sensorState | groupName state data | The sensorState command reports the current state values for a specified group of sensor. The syntax and interpretation for the state data is specific to each group. This message is sent once for each group at each sensor evaluation (normally several times per second). |
| systemError | systemError driveController | This message informs the station user of a failure in one of the robot's subsystems. The error_type argument indicates which subsystem failed, including driveController, sensorController, headHome. |
| systemInfo | systemInfo wireless 45 | This message allows regular reporting of information that falls outside the sensor system such as wireless signal strength. |
| text | text "This is some text" | The text string sends a text string from the robot to the station, where the string is displayed to the user. This message is used mainly for debugging. |
| version | version 1.6 | This message identifies the software version currently running on the robot. It is sent once at the start of the session to allow the station to do any necessary backward compatibility adjustments. |

The processor 54 of the robot high level controller 50 may operate a program that determines whether the robot 12 has received a robot control command within a time interval. For example, if the robot 12 does not receive a control command within 2 seconds then the processor 54 provides instructions to the low level controller 50 to stop the robot 12. Although a software embodiment is described, it is to be understood that the control command monitoring feature could be implemented with hardware, or a combination of hardware and software. The hardware may include a timer that is reset each time a control command is received and generates, or terminates, a command or signal, to stop the robot.

The remote station computer 22 may monitor the receipt of video images provided by the robot camera. The computer 22 may generate and transmit a STOP command to the robot if the remote station does not receive or transmit an updated video image within a time interval. The STOP command causes the robot to stop. By way of example, the computer 22 may generate a STOP command if the remote control station does not receive a new video image within 2 seconds. Although a software embodiment is described, it is to be understood that the video image monitoring feature could be implemented with hardware, or a combination of hardware and software. The hardware may include a timer that is reset each time a new video image is received and generates, or terminates, a command or signal, to generate the robot STOP command.

The robot may also have internal safety failure features. For example, the robot may monitor communication between the robot controller and the robot servo used to operate the platform motors. The robot monitor may switch a relay to terminate power to the platform motors if the monitor detects a lack of communication between the robot controller and the motor servo.

The remote station may also have a safety feature for the input device 32. For example, if there is no input from the joystick for a certain time interval (eg. 10 seconds) the computer 22 may not relay subsequent input unless the user presses a button for another time interval (eg. 2 seconds), which reactivates the input device.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

For example, although a battery recharger station has been shown and described, it is to be understood that the robot may have a conventional power cord 150 that is plugged into a conventional wall socket 152. In operation the user at the remote station can request someone at the robot site to plug the power cord 150 into the wall socket 152. The user at the remote site can unplug the power cord by moving the robot 12 away from the wall socket 152 and pulling the cord 150 out of the socket 152.

What is claimed is:

1. A remote controlled robot system, comprising:
   a remote control station that transmits a robot control command; and,
   a robot that includes a camera and moves in response to said robot control command, said robot automatically stops movement if said robot does not receive a subsequent robot control command within a time interval.

2. The system of claim 1, wherein said robot includes a processor that operates a program to determine whether said robot has received said subsequent robot control command within said time interval.

3. The system of claim 1, wherein said remote control station includes a screen that receives a video image from said camera of said robot, said remote station transmits a stop command if a subsequent video image is not received by said remote station within a time interval.

4. The system of claim 1, wherein said robot further includes a screen, a microphone and a speaker, and said remote control station includes a screen, a camera, a microphone and a speaker.

5. The system of claim 1, further comprising a broadband network that is coupled to said robot and said remote control station.

6. A remote controlled robot system, comprising:
   a remote control station that transmits a robot control command; and,
   a robot that includes a camera and moves in response to said robot control command, said robot contains means for automatically stopping said robot movement if said robot does not receive a subsequent robot control command within a time interval.

7. The system of claim 6, wherein said means includes a processor that operates a program to determine whether said robot has received said subsequent robot control command within said time interval.

8. The system of claim 6, wherein said remote control station includes a screen that receives a video image from said camera of said robot, said remote station contains means for transmitting a stop command if a subsequent video image is not received by said remote station within a time interval.

9. The system of claim 6, wherein said robot further includes a screen, a microphone and a speaker, and said remote control station includes a screen, a camera, a microphone and a speaker.

10. The system of claim 6, further comprising a broadband network that is coupled to said robot and said remote control station.

11. A method for remotely controlling a robot that has a camera, comprising:
    transmitting a robot control command from a remote control station;
    receiving the robot control command at a robot that has a camera;
    moving the robot in accordance with the robot control command; and,
    stopping movement of the robot if a subsequent robot control command is not received within a time interval.

12. The method of claim 11, wherein the remote control station receives a video image from the robot camera and the remote control station transmits a stop command to the robot if the remote control station does not receive a video image within a time interval.

13. The method of claim 11, wherein the robot control command is transmitted through a broadband network.

14. A remote controlled robot system, comprising:
    a robot that includes a camera; and,
    a remote control station that transmits a stop command to said robot if said remote control station does not receive a video image from said camera within a time interval.

15. The system of claim 14, wherein said remote control station includes a processor that operates a program to determine whether said remote control station has received said video image within said time interval.

16. The system of claim 14, wherein said robot further includes a screen, a microphone and a speaker, and said remote control station includes a screen, a camera, a microphone and a speaker.

17. The system of claim 14, further comprising a broadband network that is coupled to said robot and said remote control station.

18. A remote controlled robot system, comprising:
    a robot that includes a camera; and,
    a remote control station that contains means 7 for transmitting a stop command to said robot if said remote control station does not receive a video image from said camera within a time interval.

19. The system of claim 18, wherein said means includes a processor that operates a program to determine whether said robot has received said video image within said time interval.

20. The system of claim 18, wherein said robot further includes a screen, a microphone and a speaker, and said remote control station includes a screen, a camera, a microphone and a speaker.

21. The system of claim 18, further comprising a broadband network that is coupled to said robot and said remote control station.

22. A method for remotely controlling a robot that has a camera, comprising:
    transmitting a robot control command from a remote control station;
    receiving the robot control command at a robot that has a camera;
    moving the robot in accordance with the robot control command; and,
    transmitting a stop command to the robot if a video image is not received from the camera within a time interval.

23. The method of claim 22, wherein the robot control and stop commands are transmitted through a broadband network.

* * * * *

(12) EX PARTE REEXAMINATION CERTIFICATE (10146th)

United States Patent
Wang et al.

(10) Number: US 7,222,000 C1
(45) Certificate Issued: May 5, 2014

(54) MOBILE VIDEOCONFERENCING PLATFORM WITH AUTOMATIC SHUT-OFF FEATURES

(75) Inventors: Yulun Wang, Goleta, CA (US); Charles S. Jordan, Santa Barbara, CA (US); Marco Pinter, Santa Barbara, CA (US); Jonathan Southard, Santa Barbara, CA (US)

(73) Assignee: InTouch Technologies, Inc., Goleta, CA (US)

Reexamination Request:
No. 90/012,151, Feb. 22, 2012

Reexamination Certificate for:
Patent No.: 7,222,000
Issued: May 22, 2007
Appl. No.: 11/039,341
Filed: Jan. 18, 2005

(51) Int. Cl.
*G06F 19/00* (2011.01)

(52) U.S. Cl.
USPC ............... 700/259; 318/568.11; 318/568.12; 318/568.13; 318/568.16; 318/568.21; 318/568.25; 600/117; 600/118; 600/407; 600/426; 600/429; 600/587; 600/595; 606/1; 606/102; 606/130; 606/139; 700/245; 700/247; 700/248; 700/251; 700/257; 700/258; 700/260; 700/261; 700/262; 700/264; 901/1; 901/2; 901/27

(58) Field of Classification Search
None
See application file for complete search history.

(56) References Cited

To view the complete listing of prior art documents cited during the proceeding for Reexamination Control Number 90/012,151, please refer to the USPTO's public Patent Application Information Retrieval (PAIR) system under the Display References tab.

*Primary Examiner* — Andres Kashnikow

(57) ABSTRACT

A remote controlled robot system that includes a robot and a remote control station. A user can control movement of the robot from the remote control station. The remote control station may generate robot control commands that are transmitted through a broadband network. The robot has a camera that generates video images that are transmitted to the remote control station through the network. The user can control movement of the robot while viewing the video images provided by the robot camera. The robot can automatically stop movement if it does not receive a robot control command within a time interval. The remote control station may transmit a stop command to the robot if the station does not receive an updated video image within a time interval.

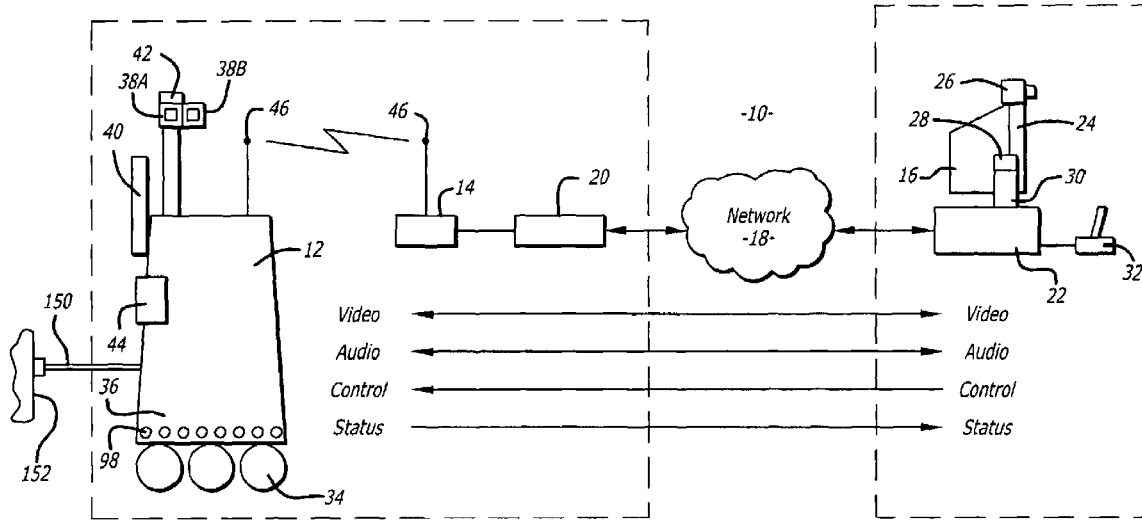

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1, 6, 11, 14, 18 and 19 are determined to be patentable as amended.

Claims 2-5, 7-10, 12, 13, 15-17 and 20-23, dependent on an amended claim, are determined to be patentable.

New claims 24-47 are added and determined to be patentable.

1. A remote controlled robot system, comprising:
   a remote control station that transmits a robot control command; and,
   a robot that includes a camera and moves in response to said robot control command, said robot [automatically stops movement] *comprising a controller that provides a stop command* if said robot does not receive a subsequent robot control command within a time interval.

6. A remote controlled robot system, comprising:
   a remote control station that transmits a robot control command; and,
   a robot that includes a camera and moves in response to said robot control command, said robot contains means for automatically stopping said robot movement if said robot does not receive a subsequent robot control command within a time interval, *said means for automatically stopping said robot comprising a controller on the robot that provides a stop command if said robot does not receive a subsequent robot control command within said time interval*.

11. A method for remotely controlling a robot that has a camera, comprising:
    transmitting a robot control command from a remote control station;
    receiving the robot control command at a robot that has a camera;
    moving the robot in accordance with the robot control command; and,
    [stopping movement of the robot] *issuing a stop command* if a subsequent robot control command is not received within a time interval.

14. A remote controlled robot system, comprising:
    a robot that includes a camera; and,
    a remote control station *comprising a computer* that transmits a stop command to said robot if said remote control station does not receive a video image from said camera within a time interval.

18. A remote controlled robot system, comprising:
    a robot that includes a camera; and,
    a remote control station that contains means [7] for transmitting a stop command to said robot if said remote control station does not receive a video image from said camera within a time interval.

19. The system of claim 18, wherein said means includes a processor that operates a program to determine whether said [robot] *remote control station* has received said video image within said time interval.

24. *The system of claim 1, wherein said remote control station and said robot connect through a satellite.*

25. *The system of claim 1, wherein said camera has a nontransmitting default state.*

26. *The system of claim 25, wherein the system includes an alert emitter on said robot, said alert indicator being operated prior to said camera transmitting video information.*

27. *The system of claim 26, wherein said alert emitter comprises a video screen, said video screen emitting a video prompt prior to said camera transmitting video information.*

28. *The system of claim 26, wherein said alert emitter comprises a speaker, said speaker emitting a sound prior to said camera transmitting video information.*

29. *The system of claim 25, wherein said robot comprises an input device that is used to initiate transmission of video images using said camera.*

30. *The system of claim 29, wherein said input device comprises a voice recognition system.*

31. *The system of claim 1, wherein said robot comprises a timer, said timer being reset with each robot control command and said robot automatically stopping if said timer reaches a preset value.*

32. *The system of claim 1, wherein said remote control station transmits a stop command if said remote control station does not receive a video image from said camera within a time interval.*

33. *The system of claim 32, wherein said remote control station comprises a timer, said timer being reset with each video image received from said camera of said robot and said remote control station transmitting said stop command if said timer reaches a preset value.*

34. *The system of claim 1, wherein said robot comprises a robot servo and a robot controller, said robot monitoring communication between said robot controller and said robot servo and terminating power to said robot servo if a lack of communication is detected between said robot controller and said robot servo.*

35. *The system of claim 1, wherein said remote control station comprises an input device, said remote control station monitors said input device and disables input after a predetermined inactivity period.*

36. *The system of claim 35, wherein said input device comprises a joystick.*

37. *The system of claim 14, wherein said remote control station and said robot connect through a satellite.*

38. *The system of claim 14, wherein said camera has a nontransmitting default state.*

39. *The system of claim 38, wherein the system includes an alert emitter on said robot, said alert indicator being operated prior to said camera transmitting video information.*

40. *The system of claim 39, wherein said alert emitter comprises a video screen, said video screen emitting a video prompt prior to said camera transmitting video information.*

41. *The system of claim 39, wherein said alert emitter comprises a speaker, said speaker emitting a sound prior to said camera transmitting video information.*

42. *The system of claim 38, wherein said robot comprises an input device that is used to initiate transmission of video images using said camera.*

43. *The system of claim 42, wherein said input device comprises a voice recognition system.*

44. *The system of claim 14, wherein said remote control station comprises a timer, said timer being reset with each*

*video image received from said camera of said robot and said remote control station transmitting said stop command if said timer reaches a preset value.*

*45. The system of claim 14, wherein said robot comprises a robot servo and a robot controller, said robot monitoring communication between said robot controller and said robot servo and terminating power to said robot servo if a lack of communication is detected between said robot controller and said robot servo.*

*46. The system of claim 14, wherein said remote control station comprises an input device, said remote control station monitors said input device and disables input after a predetermined inactivity period.*

*47. The system of claim 46, wherein said input device comprises a joystick.*

\* \* \* \* \*